(12) United States Patent
Lin et al.

(10) Patent No.: US 11,353,463 B2
(45) Date of Patent: Jun. 7, 2022

(54) REDOX-BASED REAGENTS FOR METHIONINE BIOCONJUGATION

(71) Applicant: The Regents of the University of California, Oakland, CA (US)

(72) Inventors: ShiXian Lin, Berkeley, CA (US); XiaoYu Yang, Berkeley, CA (US); F. Dean Toste, Berkeley, CA (US); Christopher J. Chang, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 62 days.

(21) Appl. No.: 16/402,113

(22) Filed: May 2, 2019

(65) Prior Publication Data

US 2019/0257838 A1  Aug. 22, 2019

Related U.S. Application Data

(63) Continuation of application No. PCT/US2017/061412, filed on Nov. 13, 2017.

(60) Provisional application No. 62/583,517, filed on Nov. 9, 2017, provisional application No. 62/421,825, filed on Nov. 14, 2016.

(51) Int. Cl.
| | |
|---|---|
| *G01N 33/68* | (2006.01) |
| *C12Q 1/26* | (2006.01) |
| *G16C 20/10* | (2019.01) |
| *G16C 20/70* | (2019.01) |
| *C12Q 1/02* | (2006.01) |
| *A61K 47/68* | (2017.01) |
| *A61K 47/64* | (2017.01) |

(Continued)

(52) U.S. Cl.
CPC ....... *G01N 33/6815* (2013.01); *A61K 47/643* (2017.08); *A61K 47/6889* (2017.08); *C07D 273/01* (2013.01); *C12Q 1/025* (2013.01); *C12Q 1/26* (2013.01); *G16C 20/10* (2019.02); *G16C 20/70* (2019.02); *C12Y 108/04013* (2013.01); *C12Y 108/04014* (2013.01); *G01N 33/58* (2013.01); *G01N 2333/47* (2013.01); *G01N 2458/15* (2013.01)

(58) Field of Classification Search
CPC .... G16C 20/10; G16C 20/70; G01N 33/6815; G01N 33/58; G01N 2458/15; G01N 2333/47; C12Q 1/025; C12Q 1/26; A61K 47/6889; A61K 47/643; C07D 273/01; C12Y 108/04014; C12Y 108/04013
See application file for complete search history.

(56) References Cited

PUBLICATIONS

Vinogradova et al. Organometallic palladium geagents for cysteine bioconjugation. Nature 2015, vol. 526, pp. 687-691. (Year: 2015 ).*

(Continued)

*Primary Examiner* — Shafiqul Haq
(74) *Attorney, Agent, or Firm* — Richard Aron Osman

(57) ABSTRACT

Chemoselective conjugation is achieved through redox reactivity by reacting an N-transfer oxidant with a thioether substrate in a redox reaction in an aqueous environment to form a conjugation product. In embodiments, Redox-Activated Chemical Tagging (ReACT) strategies for methionine-based protein functionalization. Oxaziridine (Ox) compounds serve as oxidant-mediated reagents for direct functionalization by converting methionine to the corresponding sulfimide conjugation product.

10 Claims, 2 Drawing Sheets

(51) Int. Cl.
    *C07D 273/01*     (2006.01)
    *G01N 33/58*     (2006.01)

(56) References Cited

PUBLICATIONS

Armstrong et al. Efficient nitrogen transfer from aldehyse-derived N-acyloxaziridines. Tetrahedron Letters 2003, vol. 44, pp. 5335-5338. (Year: 2003).*
Pan et al. Hydrogen exchange in native and alcohol forms of Ubiquitin. Biochemistry 1992, vol. 31, pp. 11405-11412. (Year: 1992).*
Yoshizawa et al. Dependence of ethanol effects on protein charges. International Journal of Biological Macromolecules 2014, pp. 169-172 (Year: 2014).*

* cited by examiner

REDOX-BASED REAGENTS FOR METHIONINE BIOCONJUGATION

PRIORITY

This application is a continuation of PCT/US17/61412, filed Nov. 13, 2017, which claims priority to U.S. Ser. No. 62/421,825, filed Nov. 14, 2016 and U.S. Ser. No. 62/583,517, filed Nov. 9, 2017

This invention was made with government support under Grant Numbers GM118190 and GM079465 awarded by the National Institutes of Health. The government has certain rights in the invention.

INTRODUCTION

Sulfur occupies a privileged place in biology owing to its versatile and unique chemistry.[1,2] Indeed, although cysteine and methionine are the only two sulfur-containing proteinogenic amino acids, the sulfur center plays a diverse array of critical roles spanning catalysis to metal binding to redox regulation and other post-translational modifications.[3-10] In this context, selective protein conjugation methods based on cysteine modification have enabled a broad range of fundamental and applied advances,[11-13] from probes of protein function[9,14-18] to synthesis of covalent small-molecule inhibitors[19-21] and antibody-drug conjugates[22] to activity- and reactivity-based protein profiling for functional cysteine identification[15,23,24] and inhibitor development[25]. Cysteine bioconjugation strategies typically exploit the intrinsically high nucleophilicity of the thiol/thiolate side chain, including elegant methods based on electrophilic warheads such as maleimides and alkyl and aryl halides,[26-30] transition metal-mediated bioconjugation,[31] and cysteine-to-dehydroalanine conversion.[28,29,32,33]

In contrast to the substantial body of literature on cysteine bioconjugation, analogous methods for methionine labeling remain largely underdeveloped despite a number of compelling motivations for its pursuit. Indeed, methionine is among the most hydrophobic and rare amino acids, and taken together with the fact that the majority of methionine residues are buried within interior protein cores,[1,2] surface-accessible methionines are limited and offer a potentially valuable handle for site-selective protein modification using naturally-occurring amino acid side chains. In addition, post-translational modifications of methionine, including by oxidation and/or metal binding,[3,34,35] are emerging as critical nodes in signaling pathways that control function at the cell and organism level. For example, reversible oxidation of specific methionine residues within actin can control its assembly and disassembly to serve as a navigational signal[36-38] and the antioxidant function of methionine sulfoxide reductase has been linked to regulation of life span.[39] In addition, recent work suggests that methionine oxidation can also increase binding interactions with aromatic residues within proteins.[40]

A major chemical challenge in developing a selective methionine modification reaction is its relatively weak nucleophilicity, which precludes the traditional approach of identifying an appropriate methionine-specific electrophilic partner for its acid-base bioconjugation in the presence of competing amino acids that possess stronger nucleophilicity such as cysteine, lysine, tyrosine, or serine[28,41,42.]

SUMMARY OF THE INVENTION

It is an object of the invention to provide methods and compositions for chemoselective redox conjugation to thioether substrates, and compounds and compositions comprising the conjugated substrates. The methods of the present invention are referred to as Redox Activated Chemical Tagging (ReACT).

In a first aspect, the invention provides methods for the chemoselective conjugation to a target molecule comprising one or more thioether moieties. These methods comprise reacting an N-transfer oxidant with a thioether substrate in a redox reaction in an aqueous environment to form a conjugation product.

In certain embodiments, the N-transfer oxidant comprises a reactive oxaziridine group, which reacts with at least one of the one or more thioether moieties on the target molecule, and the conjugation product comprises a resultant sulfimide on the target molecule.

In some embodiments, an N-transfer oxidant is reacted with a thioether moiety on a target molecule in an aqueous environment. Suitable N-transfer oxidants comprise an N-halide bond, a N—O bond, or an N—S bond, and preferably comprise a oxaziridine group. Suitable substrates comprise a thioether. In preferred embodiments the oxidant and thioether are represented by formulas I and II:

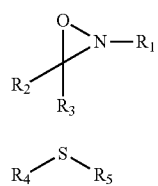

wherein $R_1$-$R_5$ are independently selected from a heteroatom and optionally substituted, optionally hetero-, optionally cyclic $C_{1-18}$ hydrocarbyl, and optionally covalently or non-covalently joined to additional atoms or moieties. In some embodiments, $R_1$ comprises a carboxyl or amide group bound to the indicated N, and further comprises a functional group (e.g., a functional group that can be reacted in a click reaction, for example, but not limited to, an azide or alkyne group), which can be further reacted to form a linker to a payload molecule comprising a corresponding functional group (e.g. a functional group that can be reacted in a click reaction, for example, but not limited to, payload molecules modified to comprise an azide or alkyne group). In some embodiments $R_1$ is —C(O)$XR_8$, X is O or NH, and $R_8$ is $C_{1-6}$ alkyl optionally substituted with $C_{2-6}$ alkynyl, $C_{2-6}$ alkynyloxy, or —$N_3$. In some embodiments, $R_2$ is H, halogen, $C_{1-6}$ alkyl, $C_{1-6}$ haloalkyl, $C_{1-6}$ alkoxy, or $C_{1-6}$ haloalkoxy, and $R_3$ is phenyl or heteroaryl, wherein phenyl or heteroaryl are optionally substituted with one or more (e.g. 1, 2, 3, 4 or 5, preferably 1, 2 or 3) substituents independently selected from the group consisting of halogen, $C_{1-6}$ alkyl, $C_{1-6}$ haloalkyl, $C_{1-6}$ alkoxy, and $C_{1-6}$ haloalkoxy. In some embodiments $R_1$ is —C(O)$XR_8$, X is O or NH, and $R_8$ is $C_{1-6}$ alkyl optionally substituted with $C_{2-6}$ alkynyl, $C_{2-6}$ alkynyloxy, or —$N_3$; $R_2$ is H, $C_{1-6}$ alkyl, or $C_{1-6}$ haloalkyl, and $R_3$ is phenyl, for compounds of formula I. In some embodiments of compounds of formula II, $R_4$ is $C_{1-6}$ alkyl and $R_5$ is substituted $C_{1-6}$ alkyl such that $R_4$—S—$R_5$ is an amino acid residue of a protein or polypeptide, preferably wherein $R_4$—S—$R_5$ is a methionine residue of protein or polypeptide. In some embodiments, $R_4$—S—$R_5$ represents a methionine thioether of a protein or polypeptide target molecule. Such proteins or polypeptides include, without limitation, a therapeutic protein or polypeptide, including an antibody or antibody fragment. In some embodiments, the protein or polypeptide includes one or more additional methionine residues that may also react with the N-transfer oxidant in the reaction with compounds of formula I. In some embodiments, the compound of formula II is a protein or polypeptide having one or more methionine residues, wherein one or more of the methionine residues reacts with the N-transfer oxidant. In some embodiments, $R_4$ is methyl and $R_5$ is —$CH_2CH_2CH(NHR_6)C(O)R_7$, wherein $R_6$ is —H or $NHR_6$ forms a peptide bond, and $R_7$ is —OH, or $C(O)R_7$ forms a peptide bond, provided that at least one of $NHR_6$ and $C(O)R_7$ forms a peptide bond.

In some embodiments, the compound of formula II is a compound of formula IIa

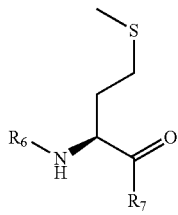

IIa wherein NH—$R_6$ and C(O)—$R_7$ are peptide bonds within a protein or peptide, or $R_6$ is —H and C(O)—$R_7$ is a peptide bond within a protein or peptide, or $R_7$ is —OH and $NHR_6$ is a peptide bond within a protein or peptide.

In another aspect, a compound of formula I is provided, where $R_1$ comprises a functional group, wherein said functional group can be further reacted to form a linker to a payload molecule, such as an active moiety. In some embodiments $R_1$ is —$C(O)XR_8$, X is O or NH, and $R_8$ is $C_{1-6}$ alkyl optionally substituted with $C_{2-6}$ alkynyl, $C_{2-6}$ alkynyloxy, or —$N_3$; $R_2$ is H, halogen, $C_{1-6}$ alkyl, $C_{1-6}$ haloalkyl, $C_{1-6}$ alkoxy, or $C_{1-6}$ haloalkoxy, and $R_3$ is phenyl or heteroaryl, wherein phenyl or heteroaryl are optionally substituted with one or more (e.g. 1, 2, 3, 4 or 5, preferably 1, 2 or 3) substituents independently selected from the group consisting of halogen, $C_{1-6}$ alkyl, $C_{1-6}$ haloalkyl, $C_{1-6}$ alkoxy, and $C_{1-6}$ haloalkoxy. In a preferred embodiment, $R_2$ is H; and $R_3$ is phenyl. In some embodiments, the compound of formula I is a compound of formula Ia

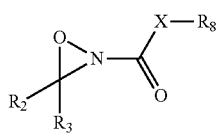

Ia wherein X, $R_2$, $R_3$ and $R_8$ are as defined for compounds of formula I. In some embodiments X is NH.

In another aspect, a compound of formula III is provided:

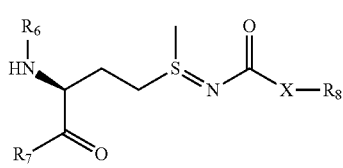

III wherein $R_6$ and $R_7$ are as defined for compounds of formula II and X and $R_8$ are as defined for compounds of formula I. In some embodiments, X is NH.

In some embodiments, the compound of formula III is a compound of formula IIIa

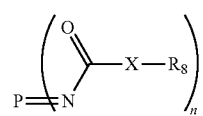

IIIa wherein P represents a polypeptide or protein linked to the indicated nitrogen via a sulfimide bond with the sulfur of methionine, wherein the polypeptide or protein has n sulfimide modified methionine residues, where n is 1 or more, including 1-20, 1-15, 1-10, 1-5, 1, 2, 3, 4 or 5, and X and $R_8$ are as defined for compounds of formula I. In some embodiments, X is NH.

In another aspect, a target molecule conjugate is provided, wherein the target molecule conjugate comprises a target molecule comprising at least one sulfimide modified methionine residue bound to a linker, wherein said linker is bound to a payload molecule. In some embodiments, the payload molecule is an active moiety. In some embodiments, the target molecule is a protein or polypeptide and the conjugate is a protein or polypeptide conjugate of formula IV

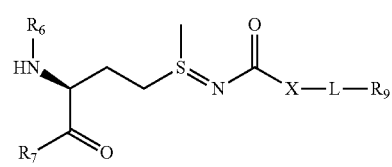

IV wherein $R_6$ and $R_7$ are as defined in formula II, X is O or NH, L is a linker moiety and $R_9$ is a payload molecule. In some embodiments, the payload molecule is an active moiety. In some embodiments, X is NH. In some embodiments L is a linker resulting from the click reaction of a compound of formula III (including a compound of formula Ina) and a suitably modified payload molecule. Suitably modified payload molecules contain substituents reactive in click reactions, for example, but not limited to, payload molecules modified to comprise an azide or alkyne group (see e.g., FIG. 3).

In some embodiments, the compound of formula IV is a compound of formula IVa

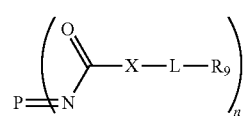

IVa wherein P represents a polypeptide or protein linked to the indicated nitrogen via a sulfimide bond with the sulfur of methionine, wherein the polypeptide or protein has n sulfimide modified methionine residues, where n is 1 or more, including 1-20, 1-15, 1-10, 1-5, 1, 2, 3, 4 or 5, X is O or NH, and L and $R_9$ are as defined for a compound of formula IV. In some embodiments, X is NH. In some embodiments L is a linker resulting from the click reaction of a compound of formula III (including a compound of formula IIIa) and a suitably modified payload molecule. In some embodiments, L comprises a triazole or isoxazole ring linking group. In some embodiments, the compound of formula IV is a compound of formula IVb $$P=(L_1\text{-}R_9)_{n_{IVb}}$$

wherein P represents a polypeptide or protein modified such that P=$L_1$ is a sulfimide bond between a methionine residue of P and linker $L_1$, wherein the polypeptide or protein has n sulfimide modified methionine residues, where n is 1 or more, including 1-20, 1-15, 1-10, 1-5, 1, 2, 3, 4 or 5, and each $L_1$ is a linker moiety comprising =N— in the sulfimide bond to a methionine sulfur within P, and $R_9$ is as defined for a compound of formula IV. In some embodiments, $L_1$ comprises a triazole or isoxazole ring linking group. In some embodiments, P is a polypeptide or protein, such as an enzyme, an antigenic protein, a chemokine, a cytokine, a cellular receptor, a ligand for a cellular receptor, or an antibody or active fragment thereof. In some embodiments, the antibody or active fragment thereof comprises a modification of the wild type antibody by introducing one or more accessible methionine residues.

In another aspect the invention provides a redox-activated chemical tagging (ReACT) method for methionine-based substrate functionalization, comprising contacting a methionine-containing substrate with an oxaziridine in an aqueous environment wherein the oxaziridine directly functionalizes the substrate by converting the methionine of a substrate to the corresponding sulfimide conjugation product. In some embodiments, the invention provides reacting a compound of formula I (including a compound of formula Ia) with a compound of formula II (including a compound of formula IIa) to form a compound of formula III (including a compound of formula IIIa). In some embodiments, the invention provides reacting a protein, such as an antibody or active fragment thereof, with a compound of formula I (including a compound of formula Ia) to provide a compound formula III (including a compound of formula IIIa). In some embodiments, the invention further provides reacting a compound of formula III (including a compound of formula IIIa) to form a compound of formula IV (including a compound of formula IVa or IVb). In some embodiments, the invention further provides reacting a compound of formula IIIa to form a compound of formula IVa or IVb, preferably wherein P is an antibody or active fragment thereof.

In some embodiments the substrate is a protein, and the method results in modification of the protein, with applications in synthesis and characterization of antibody-drug conjugates and related biologic therapeutics and imaging agents, chemoproteomics and inhibitor design, as well as modifications to study and improve upon protein function, including solubility, stability, and metabolism and pharmacokinetics.

The subject methods and ReACT methods can be combined with stable isotope labeling with amino acid in cell culture (SILAC) or isotope coded affinity tag (ICAT) for quantitative proteomics analysis of methionine function in vivo and in vitro by mass spectrometry, with application including but not limited to quantitative analysis of methionine reactivity, quantitative analysis of oxidative-sensitive methionine, quantitative analysis of stress sensitive methionine and quantitative analysis of methionine sulfoxide reductase substrates. In another aspect, the invention provides compounds adapted for use in a redox-activated chemical tagging (ReACT) method. In some embodiments, the invention provides a compound of formula I (including a compound of formula Ia); a compound of formula II (including a compound of formula IIa); or a compound of formula III (including a compound of formula IIIa).

In another aspect, the invention provides a polypeptide or protein conjugate which has the structure of formula IV (including a structure of formula IVa or IVb), wherein P is a polypeptide or protein such as an enzyme, an antigenic protein, a chemokine, a cytokine, a cellular receptor, or an antibody or active fragment thereof.

The invention encompasses all combination of the particular embodiments recited herein, as if each combination had been laboriously recited.

DESCRIPTION OF PARTICULAR EMBODIMENTS OF THE INVENTION

Figure 1A:
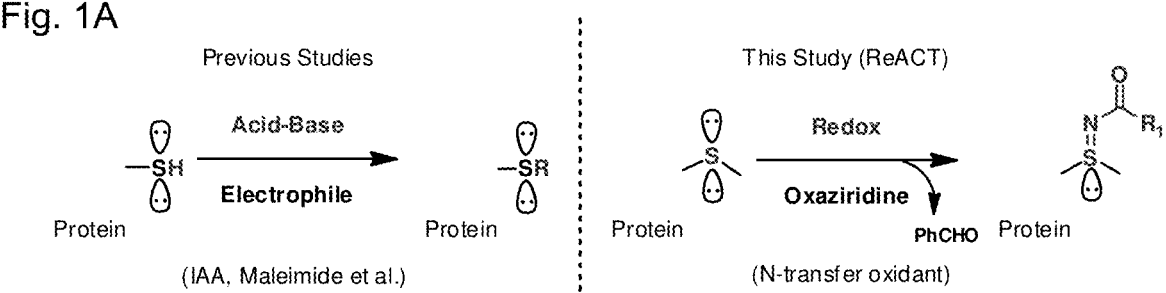
FIG. 1A-D. The ReACT strategy for chemoselective methionine bioconjugation. (A) Left panel: Acid-base conjugation strategies for cysteine-based protein functionalization; Right panel: Redox-Activated Chemical Tagging (ReACT) strategies for methionine-based protein functionalization. (B) Model redox conjugation reaction with N-acetyl-L-methionine methyl ester (S1) and various oxaziridine compounds as substrates in co-solvent. (C) Number of unique redox conjugation carrying peptide on Met, Lys and Cys. (D) Yield of conjugation reaction.

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Methionine-selective ligation reactions remain elusive owing to its intrinsically weak nucleophilicity. Here we disclose strategies for chemoselective methionine bioconjugation through redox reactivity, using oxaziridine-based reagents to achieve highly selective, rapid, and robust methionine labeling under a range of biocompatible reaction conditions. We highlight the broad utility of this conjugation method to enable precise addition of payloads to proteins including therapeutic antibody, synthesis of antibody-drug conjugates, and identification of hyper-reactive methionine residues in whole proteomes.

The invention provides many commercial applications including:

1. Therapeutic proteins functionalization based on methionine bioconjugation such as therapeutic protein PEGylation, antibody-drug conjugates, protein labeling for imaging and diagnosis, as well as other protein post translational modifications.

2. Therapeutic polypeptides functionalization based on methionine bioconjugation such as polypeptide PEGylation, polypeptide-drug conjugates and other polypeptide post-translational modifications.

3. Therapeutic intervention based on methionine bioconjugation for protein function activation and/or inhibition.

4. Biomolecule functionalization based on thioether bioconjugation using oxaziridine compounds such as DNA, RNA, lipid and sugar bioconjugations The present invention provides a unique and general redox-based approach to chemoselective methionine conjugation that complements the wealth of acid-base conjugation methods for modification of more nucleophilic amino acids such as cysteine, lysine, and serine. Three major utility directions of this invention are listed as follow:

1. One utility of the present invention is to provide for the functionalization of proteins and polypeptides, such as antibodies and their fragments, as well as other therapeutic proteins, using naturally-occurring methionine residues that are native or readily introduced by chemical modification or by standard site-directed mutagenesis. This procedure is simple and straightforward, can be applied to all proteins or polypeptides, for example to provide a chemical handle that may be used to install poly(alkyl oxide) (e.g. "PEG") moieties, fluorophores and other payloads or tracers, or to conjugate two polypeptides together (e.g., an antibody/protein conjugate).

2. More broadly, the present invention provides for installation of various payloads as mentioned above onto other biomolecules, including but not limit to, DNA, RNA, lipid and sugar by introduction a thioether function group. This method allows functionalization of any thioether containing biomolecules with a simple and straightforward procedure.

3. Finally, the selectivity of the oxaziridine as the N-transfer oxidant offers a chemical platform for identifying and studying functional methionines in whole proteomes, and function protein using methionine as key residues, providing a vehicle for therapeutic interventions based on reactive methionine activation and/or inhibition.

The present invention can provide several benefits as compared to other naturally-occurring amino acids such as cysteine, lysine and tyrosine based bioconjugation methods.

1. The present invention provides highly selective, rapid, and robust methionine labeling methodology that is operable under a range of biocompatible reaction conditions using redox based reactivity without using electrophiles to label protein, thus avoiding a selectivity issue, and a resulting inconsistency of labeling in a protein drug.

2. The relative rarity of methionine in surface-accessible forms, such as in the complementarity determining region (CDR) of antibodies that show highly similar sequence homology, significantly reduces background protein functionalization for a series of therapeutic proteins when using methodology of the present invention.

3. The present invention can permit installation of various payloads onto proteins at well-defined positions and with excellent payload-target molecule conjugation efficiency due to the extremely high reactivity of the oxaziridine group with the thioether. In certain embodiments, the protein functionalization of the present invention can be completed within 20 min at neutral pH and under biocompatible conditions. The reactivity kinetics of our method is much faster than traditional protein modification methods. This provides a significantly simplified the protein functionalization procedure.

4. The selectivity of the oxaziridine conjugation chemistry provides a platform for identifying and studying functional methionines in whole proteomes, as well as a starting point for therapeutic interventions based on reactive methionine activation and/or inhibition. This invention provides novel protein drug design methods for new drug design and discovery.

5. The bioconjugation linkages described herein are stable for at least 14 days in the presence of 100% FBS, which is beneficial for in vivo applications. The protein functionalization is also stable in an extracellular environment. More importantly, under strong thiol reducing conditions such as are found intracellularly, the linkage can be cleaved to release an attached active moiety (e.g. a therapeutic) within a cell.

The present invention also may provide significant advantages over non-natural amino acid based bioconjugation methods. The present methods enable the direct functionalization of a protein of interest at directed methionine residues without engineering the non-natural functionalities into a protein through such non-natural amino acids.

Chemistry

A hydrocarbyl group is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which comprises 1-15 carbon atoms and optionally includes one or more heteroatoms in its carbon skeleton.

The term "heteroatom" as used herein generally means any atom other than carbon or hydrogen. Preferred heteroatoms include oxygen (O), phosphorus (P), sulfur (S), nitrogen (N), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, isocyanate, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. $C_{2-8}$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. $C_{2-8}$ means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —CH$_2$—CH$_2$—CH$_2$—CH$_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, e.g. "haloalkoxy" refers to a haloalkyl group attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, P, Si and S, wherein the nitrogen, sulfur, and phosphorous atoms may optionally be oxidized and the nitrogen heteroatom may optionally be quaternized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH3)-CH$_3$. Up to two heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent means a divalent radical derived from heteroalkyl, as exemplified by —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., $C_{3-8}$ means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "$C_{1-4}$haloalkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "$C_{1-4}$perhaloalkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'OR", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR'", —NR"CO$_2$R', —NH—C(NH$_2$)=NH, —NR'C(NH$_2$)=NH, —NH—C(NH$_2$)=NR', —S(O)R', —SO$_2$NR'R", —NR"SO$_2$R, —CN and —NO$_2$, in a number ranging from zero to three, with those groups having zero, one or two substituents being particularly preferred. R', R" and R''' each independently refer to hydrogen, unsubstituted C$_{1-8}$ alkyl and heteroalkyl, unsubstituted aryl, aryl substituted with one to three halogens, unsubstituted alkyl, alkoxy or thioalkoxy groups, or aryl-C$_{1-4}$ alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R''', —OC(O)R', —C(O)R', —CONR'R", —OC(O)NR'R", —NR"C(O)R', —NR"CO$_2$R', —NR'—SO$_2$NR"R''', —S(O)R', —SO2R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R''', —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO$_2$R', —NR'—C(O)NR"R''', —NR'—SO$_2$NR"R''', —NH—C(NH2)=NH, —NR'C(NH$_2$)=NH, —NH—C(NH$_2$)=NR', —S(O)R', —SO$_2$R, —SO$_2$NR'R", —NR"SO$_2$R, —N$_3$, —CH(Ph)$_2$, C$_{1-4}$ perfluoroalkoxy and C$_{1-4}$ perfluoroalkyl, in a number ranging from zero to the total number of open valences on the aromatic ring system; and where R', R" and R''' are independently selected from hydrogen, C$_{1-8}$ alkyl and heteroalkyl, unsubstituted aryl and heteroaryl, (unsubstituted aryl)-C$_{1-4}$ alkyl and (unsubstituted aryl)oxy-C$_{1-4}$ alkyl. When the aryl group is 1,2,3,4-tetrahydronaphthalene, it may be substituted with a substituted or unsubstituted C$_{3-7}$ spirocycloalkyl group. The C$_{3-7}$ spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R, —N$_3$, —CH(Ph)$_2$, C$_{1-4}$ perfluoroalkoxy and C$_{1-4}$ perfluoroalkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, C$_{1-4}$ perfluoroalkoxy and C$_{1-4}$ perfluoroalkyl.

The substituent —CO$_2$H, as used herein, includes bioisosteric replacements therefore; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH$_2$)q-U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)s-X—(CH$_2$)t-, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, optionally heteroatom C$_{1-6}$ alkyl, substituted or unsubstituted, optionally heteroatom C$_{2-6}$ alkenyl, substituted or unsubstituted, optionally heteroatom C$_{2-6}$ alkynyl, or substituted or unsubstituted, optionally heteroatom C$_{6-14}$ aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, isocyanate, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF$_3$).

The term "peptide" as used herein refers to at least two amino acids joined by peptide bonds. A "polypeptide" refers to a short sequence of amino acids (less than 50), where the amino acids are connected to each other by peptide bonds. A peptide or polypeptide may occur free or bound to another moiety, such as a macromolecule, lipid, oligo- or polysaccharide, and/or a polypeptide. Where a peptide is incorporated into a polypeptide chain, the term "peptide" may still be used to refer specifically to the short sequence of amino acids. A peptide or polypeptide may be connected to another moiety by way of a peptide bond or some other type of linkage. A polypeptide is more than two amino acids in length and generally less than about 25 amino acids in length. The terms "peptide" and "oligopeptide" may be used interchangeably.

"Protein" generally refers to the sequence of amino acids comprising a polypeptide chain and that is greater than 50 amino acids in length. Protein may also refer to a three dimensional structure of the polypeptide. "Denatured protein" refers to a partially denatured polypeptide, having some residual three dimensional structure or, alternatively, to an essentially random three dimensional structure, i.e., totally denatured. The invention encompasses reagents of, and methods using, polypeptide variants, e.g., involving glycosylation, phosphorylation, sulfation, disulfide bond formation, deamidation, isomerization, cleavage points in signal or leader sequence processing, covalent and non-covalently bound cofactors, oxidized variants, and the like. The formation of disulfide linked proteins is described (see, e.g., Woycechowsky and Raines (2000) Curr. Opin. Chem. Biol. 4:533-539; Creighton, et al. (1995) Trends Biotechnol. 13:18-23).

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g., Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The term "cytokine" as used herein means any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Interleukin-8 (IL-8), Tumor Necrosis Factor-alpha (TNF-a) and Tumor Necrosis Factor-beta (TNF-b).

The term "receptor" as used herein refers to a molecule, typically composed primarily of protein, that binds to a cognate ligand and that is associated, or derived from, a cell, and usually one or more types of cellular membranes, and has as its main biological function the ability to bind a specific ligand or group of ligands, and, upon ligand binding, to mediate signal transduction, either directly or indirectly, in the cell. One type of receptor has three portions or domains, namely, an intracellular domain, an extracellular domain, and a transmembrane domain. In addition, the receptor typically has a sequence of about 5-25 amino acids at its amino terminus that serve to target the receptor to the proper membrane. These domains will vary in size and in function from receptor to receptor. Typically, the extracellular domain binds to one or more ligands, the transmembrane domain anchors the receptor into the membrane, and the intracellular domain perceives the binding of ligand and transmits a signal to the interior of the cell (the intracellular environment).

The term "chemokine" as used herein refers to a member of one of 4 different structural families, comprising over 50 ligands that interact with at least 17 different receptors These chemokine families, named according to the structure of a conserved cysteine-containing motif, are defined by the presence of either a C, a CC, a CXC, or a C'C at their amino terminus of the protein. The term "amino acid peptide", e.g. as used in describing compounds of formula II (including a compound of formula IIa) refers to the bonds within a protein or polypeptide, wherein the thioether containing substrate includes an amino acid peptide, e.g. is part of an amino acid residue of a polypeptide or protein, in a preferred embodiment, the thioether is within a methionine residue of a polypeptide or protein. As such, the substrate $R_4$—S—$R_5$ represents e.g. a thioether wherein $R_4$ and $R_5$ are alkyl groups, and the alkyl group of $R_5$ is substituted at one carbon with both the —NHC(O)R, and —C(O)NHR' groups within a polypeptide or protein (e.g. where R is an additional peptide chain or a carboxyl terminus OH and R' is an additional peptide chain or an amino terminus H). As such, an alkyl group, e.g. of $R_5$, substituted with an amino acid peptide can be represented as

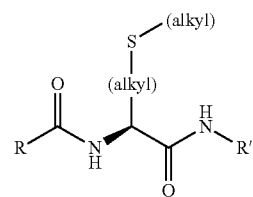

or in the preferred embodiment where the substrate $R_4$—S—$R_5$ represent a methionine residue within a protein or polypeptide, can be represented as

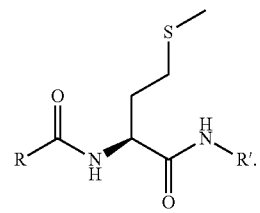

It is also understood that the substrate may comprise a polypeptide or protein that has additional modifications, or may have additional methionine residues that can be reacted by the methods of the present invention as described herein.

An "active moiety" is a payload molecule as described in the present invention, wherein said moiety conjugated to e.g. a protein or polypeptide provides some activity. The activity of the moiety includes, but is not limited to, a biological activity (e.g. a pharmaceutically active moiety, such as a small molecule pharmaceutical or a biomolecule, such as DNA, RNA, lipid or sugar), a detectable label (e.g. fluorophore, imaging label or the like), a property modifying moiety (e.g. PEGylation moiety), a sulfhydryl-specific functional moiety such as a maleimide, alkyl or aryl halide, α-haloacyl, or pyridyl disulfides, an amine-specific functional moiety such as a carbodiimide, a non-selective reactive moiety such as a photoaffinity group, an arginine-specific functional moiety such as a glyoxal, etc.

The term "click chemistry" or "click reaction" refers to well-known, selective methods of conjugation, wherein two components comprising a click reactive functional group are reacted to link the two components. For example, for the sulfimide modified peptides, polypeptides or proteins as described herein, the modified group further comprises a first click reactive functional group, and the payload molecule is suitably modified to comprise a second click reactive functional group, which is reactive with the first click reactive functional group. The click reactive functional group includes, without limitation, an azide group, a nitrone group or an alkyne group. In some embodiments click chemistry comprises reaction of an azide group with an alkyne group to form a triazole group linking the two components, or the reaction of a nitrone group with an alkyne group to form an isoxazoline group linking the two components. In some embodiments, the alkyne group is a dibenzocyclooctyne (DBCO) group or a difluorooctyne (DIFO) group. In some embodiments, the click chemistry is Copper(I)-catalyzed azide-alkyne cycloaddition (CuAAC), strain-promoted azide-alkyne cycloaddition (SPAAC) or strain-promoted alkyne-nitrone cycloaddition (SPANC). See also Jewett, John C. and Bertozzi, Carolyn, R., Cu-free click cycloaddition reactions in chemical biology. Chem Soc Rev. 39(4), 1272-1279 (2010); Agard et al., A Comparative Study of Bioorthogonal Reactions with Azides. ACS Chem. Biol., 1(10), 644-648 (2006); MacKenzie et al., Strain-promoted cycloadditions involving nitrones and alkynes—rapid tunable reactions for biorthogonal labeling. Current Opinion in Chemical Biology 21, 81-88 (2014), the disclosures of which are hereby incorporated by reference in their entirety.

Figure 1B:
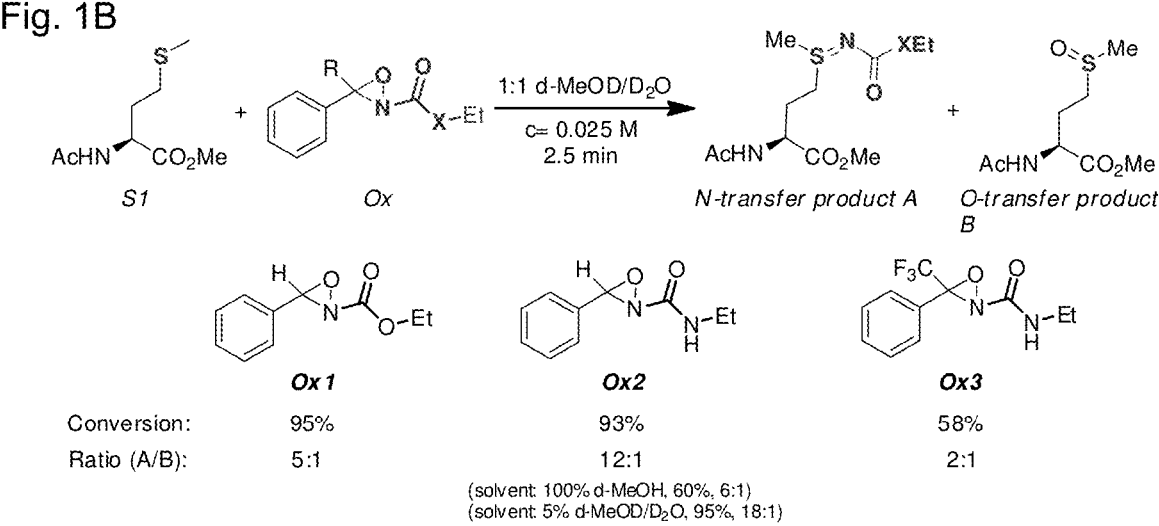

Examples; Design:

A variety of sulfur imidation reactions with methionine derivative S1 as a model substrate were screened in 1:1 d-MeOD/D$_2$O solvent using $^1$H NMR analysis of substrate conversion and reaction selectivity between the desired N-transfer product (NTP, sulfimide) and unwanted O-transfer product (OTP, sulfoxide) (FIG. 1B). A strain-driven sulfur imidation of methionine using oxaziridine 1 (Ox1) as the sulfur imidation reagent afforded 95% conversion of S1 within 2.5 min without additional catalyst with a NTP:OTP ratio of 5:1 (FIG. 1B). From this starting point, altering the linkage of the probe from carbamate to urea (Ox2) resulted in enhanced selectivity (NTP:OTP=2:1) with comparable conversion, whereas further substitution of the benzylic hydrogen of Ox2 with an electron withdrawing CF$_3$ group (Ox3) resulted in much lower selectivity (NTP:OTP=2:1) and reaction conversion (58%). Interestingly, a marked improvement in NTP:OTP selectivity from 6:1 to 18:1 was observed by increasing the percentage of water in the solvent medium from 0% to 95% (FIG. 1B), presaging the utility of this ligation reaction in biological environments.

Figure 1C:
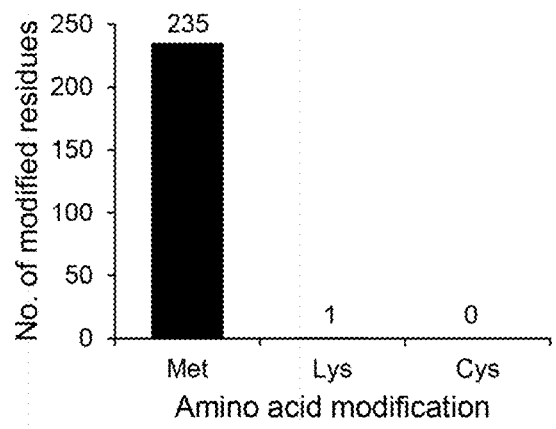

The reactivity of oxaziridine probes with other biologically relevant amino acid competitors was evaluated. In all cases, no conjugation products were observed with any of the other amino acids tested and only methionine gives a ligated product with the ReACT reagent. As a further demonstration of the high selectivity of ReACT for methionine conjugation, sites of probe labeling within a whole proteome were identified using LC-MS/MS analysis. HeLa cell lysates were treated with Ox4, trypsin digested, and then analyzed by LC-MS/MS for probe modification on all nucleophilic amino acids using the X!Tandem program[43]. Labeling of 235 methionine residues and a single lysine residue were found, with no other modifications detected on cysteine side chains or other nucleophilic amino acids (FIG. 1C). These experiments demonstrate fast kinetics of the ReACT strategy as well as near perfect selectivity for methionine residues from the single protein to whole proteome level under mild biocompatible conditions. Finally, the chemical stability of the sulfimide methionine conjugation product was tested, finding that this linkage is resistant to acidic and basic conditions, elevated temperature, as well as treatment with a strong protein disulfide reducing agent such as tris(2-carboxyethyl)phophine (TCEP).

FIG. 1A Left panel: Acid-base conjugation strategies for cysteine-based protein functionalization; Right panel: Redox-Activated Chemical Tagging (ReACT) strategies for methionine-based protein functionalization. Oxaziridine (Ox) compounds serve as oxidant-sulfimide conjugation product. (B) Model redox conjugation reaction with 25 µM of N-acetyl-L-methionine methyl ester (Si) and 27.5 µM of various oxaziridine compounds as substrates in co-solvent. (C) Number of unique redox conjugation carrying peptide on representative amino acid, namely Met, Lys and Cys by labeling HeLa cell lysate with Ox4 at the final concentration of 1 mM for 10 min. (D) Yield of conjugation reaction was performed with 15 µM of BSA carrying 4 methionine per protein and 100 µM Ox4 at indicated time point as measured by in-gel fluorescence imaging.

Application:

1. Precise Addition of Payloads to Proteins

Figure 1D:
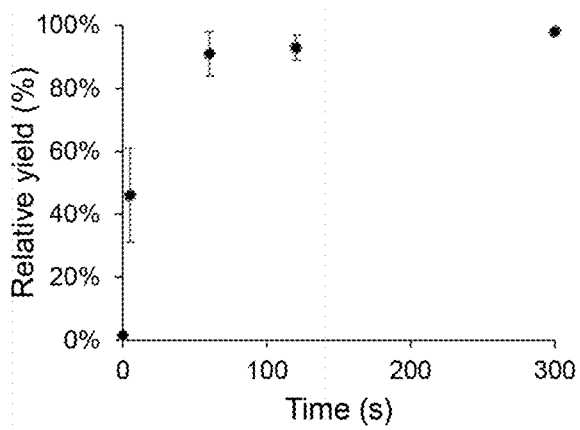
Figure 2A:
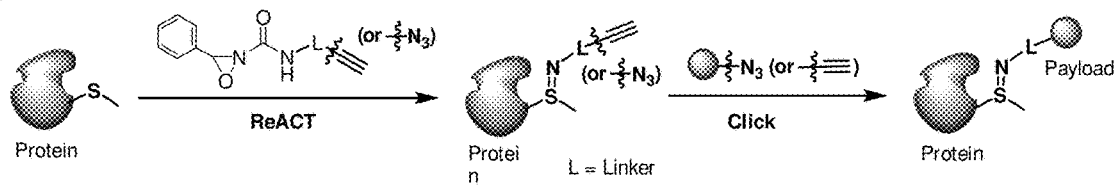
FIG. 2A-B. The ReACT strategy for protein functionalization. (A) General two-step procedure for methionine-specific protein functionalization a combination of ReACT and click reactions. (B) Redox conjugation of a CaM model protein with various oxaziridine (Ox) compounds.
Figure 2B:
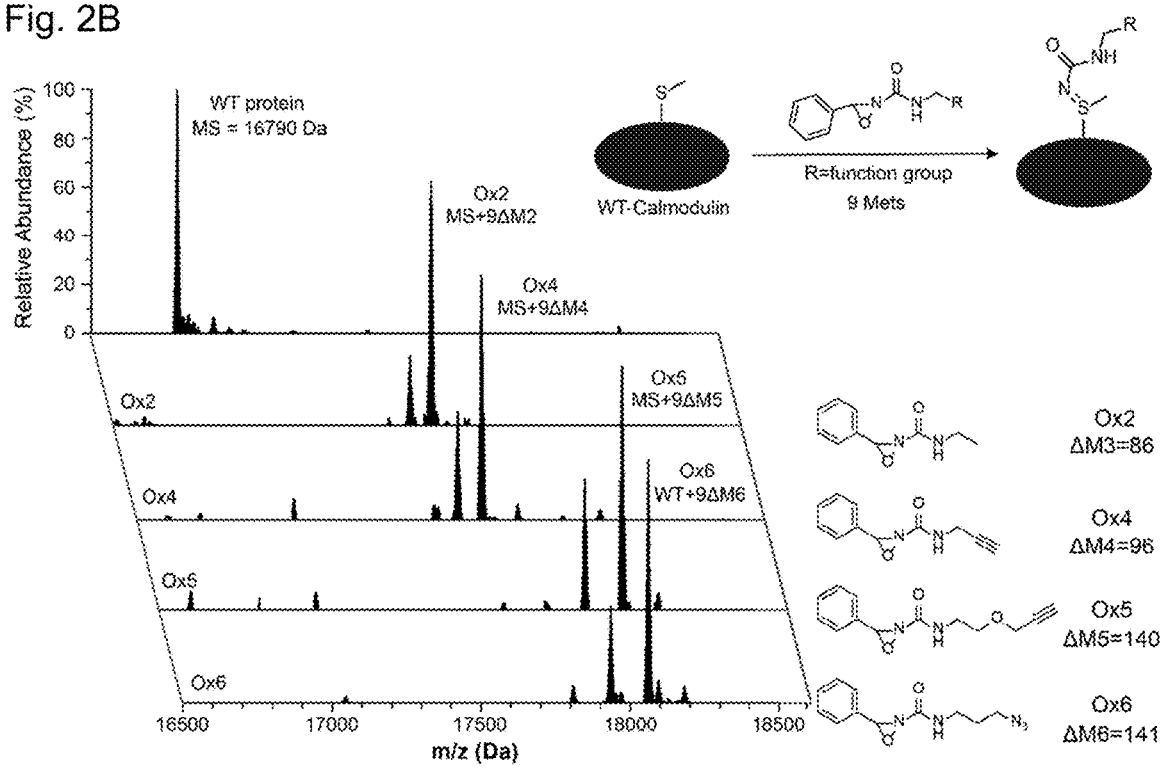

ReACT as a method for site-selective methionine conjugation of proteins was evaluated. Starting with bovine serum albumin (BSA) as a model protein using a two-step labeling protocol, BSA was first treated with oxaziridine probe Ox4 bearing a bioorthogonal alkyne group and then subsequently coupled to Cy3-azide through a copper-catalyzed azide-alkyne cycloaddition (CuAAC) reaction. The resulting redox conjugation yield to BSA was analyzed by in-gel fluorescence imaging. ReACT proceeds rapidly and can be completed with a yield >95% within 1-2 min, with 50% of labeling occurring within the first 5 s following the addition of Ox4 to the protein under standard reaction conditions (FIG. 1D). This shows that the ReACT method could enable installation of various payloads onto a protein of interest at defined methionine sites, serving as a unique method for functionalization using naturally occurring amino acids (FIG. 2A). The reactivity of various alkyne- and azide-containing oxaziridine probes with CaM model protein was assessed (FIG. 2B). LC-MS results show that ReACT enables near quantitative installation of these bioorthogonal handles on all 9 native methionine residues within 10 min of labeling time at room temperature, with a 25:1 selectivity over the only other observed minor CaM product bearing 8 sulfimide modifications (NTP) and 1 sulfoxide modification (OTP) (FIG. 2B).

FIG. 2A General two-step procedure for methionine-specific protein functionalization a combination of ReACT and click reactions. Various payloads can be installed through methionine conjugation at a directed position on a given protein. (B) Redox conjugation of a CaM model protein (100 µM) with various oxaziridine (Ox) compounds (1 mM). The chemical structures of oxaziridine probes are shown with molecular weight changes (ΔM) listed for the corresponding modifications. The deconvoluted MS data of full protein peaks are plotted in the same figure. For Ox2 labeled protein: expected mass 17,564 Da, found 17,565 Da; Ox4 labeled protein: expected mass 17,654 Da, found 17,654 Da; Ox5 labeled protein: expected mass 18,050 Da, found 18,051 Da; Ox6 labeled protein: expected mass 18,059 Da, found 18,060 Da.

Figure 3:
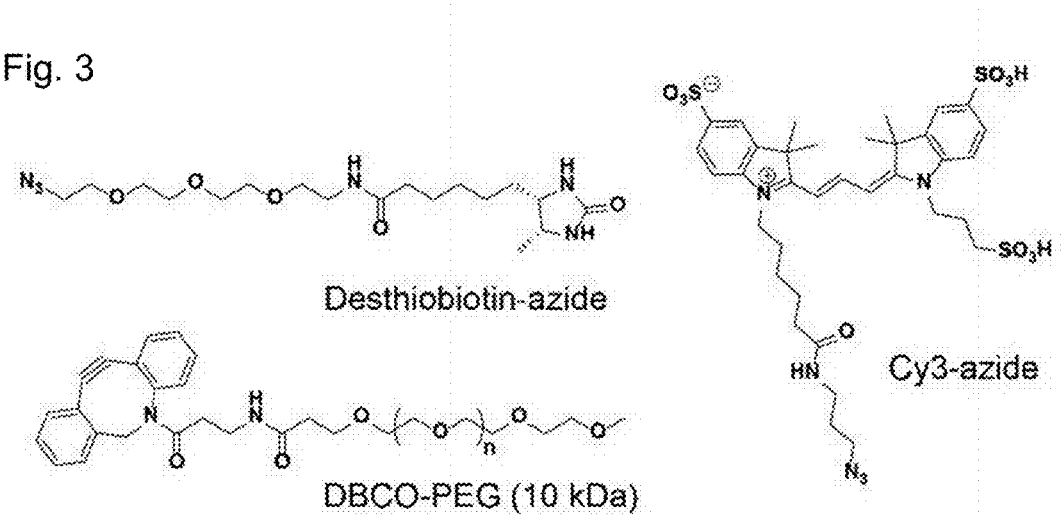
FIG. 3. Functionalization of ReACT labeled calmodulin protein with various payloads using click reaction. Desthiobiotin, Cy3 and PEG payloads comprising reactive groups suitable for conjugation using click chemistry.

Further functionalizations with biotin, fluorophore and polyethylene glycol (PEG) payloads proceed smoothly. FIG. 3. Chemical structures of Desthiobiotin-azide, Cy3-azide and Dibenzocyclooctyl(DBCO)-PEG (10 kDa). Ox4 labeled CaM proteins (40 µM) were reacted with Desthiobiotin-azide (100 µM) (B) and Cy3-azide (100 µM) (C) using CuAAC reaction. The reactions were quenched by adding BCS (1 mM), desalted three times, and analyzed by protein MS. The deconvoluted MS indicated conjugation of 1-3 biotin or Cy3 into Cam proteins using ReACT-Click, and Ox6 labeled CaM proteins (40 μM) were reacted with indicated concentration of DBCO—PEG (10 kDa) at room temperature for 8 h. The reactions were analyzed by protein gel. The high methionine reactivity and specificity of ReACT coupled with the ready availability of click reaction partners provides a straightforward method for precise protein functionalization based on this naturally occurring amino acid.

2. Antibody-Drug Conjugates

The synthesis of antibody-drug conjugates (ADCs), was studied using the anti-green fluorescent protein antibody fragment (GFP-Fab) as a starting model. Although the Fab scaffold possesses one native methionine residue on its light chain and two native methionine residues on its heavy chain, none of these side chains are surface accessible and thus cannot be labeled by ReACT, even with high oxaziridine probe loadings. As such, because these native methionines are buried within the hydrophobic interior core, ReACT offers a potentially valuable strategy for antibody bioconjugation as there is no background labeling of the wildtype antibody and subsequent engineering of surface accessible methionine sites can enable precise antibody functionalization at directed locations. Using the THIOMab platform,[44] this approach was demonstrated by replacing heavy chain (HC)-A114 or light chain (LC)-V205 residues with methionine, which showed efficient labeling with ReACT. In addition, the rapid, near-quantitative, and site-specific C-terminal labeling with ReACT on a GFP-Fab bearing a C-terminal methionine (GFP-Fab-CM) was demonstrated. Importantly, the resulting azide-carrying GFP-Fab (GFP-Fab-$N_3$) retained similar binding affinity to the GFP ligand compared to the wildtype Fab. Click reactions enable further functionalization of GFP-Fab-$N_3$ with biotin, fluorophore and drug payloads. Moreover, the resulting conjugates are compatible with biological environments. For example, an HEK-293T cell line with a doxycycline (Dox) inducible cell surface GFP expression system was used, where Dox treatment results in expression of GFP localized to the cell surface. Upon pre-addition of Dox followed by incubation with Cy3-labeled GFP-Fab made by ReACT, excellent co-localization of Cy3 and GFP signals in live HEK-293T cells was observed. In contrast, no Cy3 signal was observed in control cells without Dox addition. Furthermore, the intensity of the Cy3 signal was found to be stable for at least 14 days in the presence of 100% fetal bovine serum (FBS). Taken together, these data demonstrate that ReACT can enable antibody functionalization at directed positions with a wide variety of payloads and simultaneously retain their function for ligand binding.

ReACT was also applied to a therapeutic conjugate, Herceptin-Fab (Her-Fab). ReACT does not label wildtype Her-Fab owing to its lack of surface accessible methionines. By engineering Her-Fab platforms carrying one or two methionine residues at the C-terminus, ReACT affords quantitative conjugation with one or two redox modifications, respectively. The data establish that ReACT can enable synthesis of ADCs with a defined drug-to-antibody ratio (DAR) in excellent purity, which remains a significant challenge for bioconjugation methods employing cysteine or lysine ligation. Moreover, the bioorthogonal azide or alkyne handle introduced by methionine conjugation can be readily functionalized with additional payloads. Indeed, the ADC synthesized by linking monomethyl auristatin E (MMAE) to Her-Fab exhibits a 5-fold increase in toxicity to Her2-positive BT474 breast cancer cells compared to either wildtype Her-Fab or a mixture of wildtype Her-Fab and free MMAE, demonstrating its utility in a biological context (See Lin et al., Redox-based reagents for chemoselective methionine bioconjugation. Science 355, 597-602 (2017), the disclosure of which is hereby incorporated by reference in its entirety).

3. Reactive Methionine Profiling

ReACT may be used as a unique methionine-targeted warhead for chemoproteomics applications, owing to its high specificity and reactivity, as well as its small size for accessing a broad range of proteins. To this end, ReACT was applied to probe reactive methionines in the proteome through tandem orthogonal proteolysis—activity based protein profiling (TOP-ABPP).[45] Through dose-dependent treatment of cells with low, medium, and high levels of ReACT probe Ox4, it was attempted to identify hyper-reactive methionines that should be enriched with low-dose labeling along with less reactive methionine sites. By performing parallel TOP-ABPP (n=2 for all three groups) in HeLa cell lysates, 116 (low dose), 458 (medium dose) and 1118 (high dose) peptides that carry the desired ReACT methionine modification were identified.

Of particular interest are the hyper-reactive methionine targets, as they can predict sites of methionine-regulated protein function. This unbiased ReACT approach not only enables characterization of previously studied redox-sensitive methionines in whole proteome settings, but more importantly identifies new functional methionine sites. As a positive control, three hyper-reactive methionines within actin were identified, including Met 44 and Met 46, whose redox activities have been previously shown to play a central role in controlling actin polymerization in living cells.[36-38] With these data validating the ReACT method in hand, it was attempted to identify and characterize new targets with methionine-dependent function. As one representative example, three hyper-reactive methionine residues were found on enolase, a central enzyme in the ancient and conserved metabolic pathway of glycolysis,[46] which is of importance in regulating diseases such as cancer via the Warburg effect.[47] Included is a Met 169 residue that is highly conserved from yeast to mammals (corresponding to Met 171 on yeast enolase 1). Met 169 is close to the enzyme active site and can be oxidized along with other methionine residues in the mammalian protein upon oxidant treatment.

To characterize the functional significance of this oxidation-sensitive methionine in enolase in more detail, a yeast homolog for in vitro biochemistry studies was cloned and purified. Treatment of the wildtype yeast enolase 1 with hypochlorite resulted in a decrease in enzymatic activity with concomitant oxidation of methionine residues, including Met 171, on the protein. A similar decrease in protein activity was observed upon oxidation of the M37 IL mutant. In contrast, the activity of the M171L mutant was unaffected by oxidant treatment under the same conditions, suggesting that this highly conserved residue is critical for redox regulation of enolase function. Kinetics measurements of the wildtype and M171L mutants with and without oxidant treatment reveal that both $k_{cat}$ and $K_m$ are affected in the wildtype upon oxidation, but that these values for the M171L mutant remain the same. To show the physiological consequences of this methionine-based redox regulation at the cellular level, yeast strains were generated with a double enolase 1 and enolase 2 knockout background[48] and re-introduced either wildtype enolase 1 or the M171L mutant. The strain carrying the M171L mutation was found to be more resistant to oxidative stress-induced cell death compared to the strain with wildtype enolase 1, establishing that this methionine residue indeed serves a functional redox-active role in vivo.

References include sulfur's central role in biological processes (52-56), selective protein conjugation methods based on cysteine and their applications (57-64), existing methionine labeling methods with acid-base mechanism (65-67), and reviews on oxaziridine chemistry (68-69).

Detailed Methods

ReACT labeling of protein and cell lysate. Protein samples (BSA, calmodulin and Fab) were diluted to 1 mg/mL solution in PBS (pH=7.4). Samples were labeled with 1.1-10 equivalents of oxaziridine probe (100× stock in DMF). The ReACT labeling reactions were performed at room temperature for 10 min with agitation and immediately quenched by desalting twice with Bio-Spin Chromatography Columns (Bio-Rad). Labeled proteins were subjected to SDS-PAGE and LC-MS analysis. Proteome samples in radio immunoprecipitation assay buffer (RIPA) were labeled with the same protocol used for model protein samples. Samples were subsequently quenched by protein precipitation with cold methanol. The pellets were washed twice with cold methanol, air dried and solubilized with 2% SDS/PBS.

Procedures for click reactions. Oxaziridine labeled protein or proteome samples carrying alkyne handles at the concentration 1 mg/mL in PBS were labeled with the CuAAC reaction. The reactions were performed by addition of 1 mM $CuSO_4$ (100× stock in water), 100 µM Tris (benzyltriazolylmethyl)amine (TBTA, 100× stock in DMSO), 100 µM azide-PEG3-biotin or azide-Cy3 (100× stock in DMSO, Click Chemistry Tools) and 2 mM sodium ascorbate (100× stock in water). The reactions were then agitated for 1 hour at room temperature before quenching with 5 mM disodium bathocuproine disulfonate (BCS, 100× stock in water). Protein samples carrying azide handles at the concentration 1 mg/mL in PBS were labeled with dibenzocyclooctyne (DBCO) containing compounds using copper-free click reaction. The reactions were performed by addition of 2-10 equivalents of DBCO-Biotin, DBCO-Cy3, DBCO-PEG-10 kDa or DBCO-MMAE and reacted for 8 hour at room temperature before quenching by protein desalting.

LC-MS analysis of protein modifications. Mass spectrometry measurements of CaM and Her-Fab were obtained at QB3/Chemistry Mass Spectrometry Facility at the University of California, Berkeley. CaM modifications were analyzed on a LTQ FT mass spectrometer (Thermo Fisher Scientific) that was equipped with an electrospray ionization (ESI) source. Protein samples were directly infused using ESI in the positive ion mode in a solution (1:1 acetonitrile:water, 1% formic acid, V/V) at the rate of 5 µL/min Data acquisition was controlled using Xcalibur software (version 2.0.7, Thermo) and mass spectral deconvolution was performed using ProMass software (version 2.5 SR-1, Novatia). Her-Fab modifications were analyzed in the positive ion mode on a Synapt G2-Si mass spectrometer that was equipped with an ionKey ESI source and C4 ionKey (150 µm inner diameter, 50 mm length, 300 Å pore size, 1.7 µm particle size) and connected in line with an Acquity M-class liquid chromatograph (Waters). Mass spectrometry measurements of GFP-Fab were obtained at the University of California, San Francisco. GFP-Fab modifications were analyzed in the positive ion mode on a Xevo G2-XS mass spectrometer equipped with a LockSpray (ESI) source and Acquity Protein BEH C4 column (2.1 mm inner diameter, 50 mm length, 300 Å pore size, 1.7 µm particle size) connected in line with an Acquity I-class liquid chromatograph (Waters). Mass spectral deconvolution was performed using the maximum entropy (MaxEnt) algorithm in MassLynx software (version 4.1, Waters).

Reactive methionine profiling. HeLa cell lysates at the concentration 1 mg/mL in RIPA buffer (1 mL each) were labeled with 10 µM (low dose, 200× stock in DMF), 50 µM (medium dose, 200× stock in DMF) or 250 µM (high dose, 200× stock in DMF) Ox4 probe. Since the reaction was close to saturated with 250 µM probe by In-gel fluorescent imaging assay, 250 µM was used as t h e high dose group; and since previous literature applied 10 µM probe for the hyperreactive cysteine profiling, 10 µM probe was used as the low dose group.

The ReACT labeling reactions were performed at room temperature for 10 min and quenched by desalting twice to remove free oxaziridine probes. The CuAAC reactions were performed on the labeled protein with aforementioned method using 200 µM acid-cleavable biotin azide probe (200× stock in DMSO).(40, 41) Samples were precipitated and washed with cold methanol and dissolved in 250 µL of 2% SDS/PBS. The solutions were diluted to 5 mL with 1% triton X-100/PBS. The solutions were then added with 2 mg of streptavidin-coated magnetic beads (Promega Corporation) overnight at 4° C. with agitation. The magnetic beads were washed with 1% triton X-100/PBS (5 mL), PBS (5 mL), 6 M urea (5 mL) and PBS (5 mL).

The washed beads were then reduced with 5 mM TCEP at 65° C. for 15 mM and alkylated with 10 mM iodoacetamide (IAA) at 37° C. for 30 mM On-beads trypsin (2 µg each sample) digestion were performed at 37° C. for 16 hour. The beads were then pelleted and washed with PBS (2×2 mL), water (2×2 mL). Modified peptides on the magnetic beads were cleaved using 1% formic acid/water (2×500 µL) at room temperature for 30 mM and subsequently cleaved with 1% formic acid+50% acetonitrile/water (2×500 µL) with agitation for 30 mM The eluents were combined and concentrated with a vacuum concentrator. Peptide samples were desalted by Pierce™ C18 Spin Columns (Thermo Fisher Scientific) and kept at −20° C. until analysis.

Determination of kinetic rate constants for sulfur imidation. Rate constants k for Ox2 was measured under pseudo first order conditions with a 5- to 40-fold excess of N-acetyl-L-methionine in PBS buffer by following the exponential growth in UV absorbance of the benzaldehyde at 250 nm over time under kinetics model of UV-vis (Agilent Technologies). Stock solutions were prepared for Ox2 (200 µM) and N-acetyl-L-methionine (1 mM, 2 mM, 4 mM, and 8 mM) in PBS buffer and kept at 25° C. with water bath. Mixing equal volumes of the prepared stock solutions, corresponding to 5 to 40 equivalents of N-acetyl-L-methionine. Spectra were recorded using the following instrumental parameters: 250 nM; 10 data points per second. The UV absorbance was monitored by UV-vis under kinetics model. Data were fit to a single-exponential equation to get the observed rates k' under indicated concentration of N-acetyl-L-methionine. The observed rates k' calculated from different concentration of N-acetyl-L-methionine were plotted against the concentration of N-acetyl-L-methionine to obtain the rate constant k from the slope of the plot.

LC-MS/MS analysis of peptide modifications. Trypsin digested peptides were analyzed by LC-MS/MS on a Thermo Scientific Q Exactive Orbitrap mass spectrometer in conjunction with a Proxeon Easy-nLC II HPLC (Thermo Fisher Scientific) and Proxeon nanospray source. The digested peptides were loaded a 100 micron×25 mm Magic C18 100 Å 5U reverse phase trap where they were desalted online before being separated with a 75 micron×150 mm Magic C18 200 Å 3U reverse phase column. Peptides were eluted using a 120 min gradient with a flow rate of 300 nL/min. An MS survey scan was obtained for the m/z range of 300-1600; MS/MS spectra were acquired using a top 15 method, where the top 15 ions in the MS spectra were subjected to High Energy Collisional Dissociation (HCD). An isolation mass window of 1.6 m/z was used for the precursor ion selection, and normalized collision energy of 27% was used for fragmentation. Five second duration was used for the dynamic exclusion.

Peptide modification identification. Tandem mass spectra were extracted and charge state deconvoluted by Proteome Discoverer (Thermo Fisher Scientific). All MS/MS samples were analyzed using X! Tandem (The GPM, thegpm.org; version TORNADO (2013.02.01.1)). X! Tandem was set up to search Uniprot Human database (version 11/14/2015, 140248 entries), the cRAP database of common laboratory contaminants (www.thegpm.org/crap; 114 entries) plus an equal number of reverse protein sequences assuming the digestion enzyme was trypsin. X! Tandem was searched with a fragment ion mass tolerance of 20 PPM and a parent ion tolerance of 20 PPM. IAA derivative of cysteine was specified in X! Tandem as a fixed modification. Modification of +197.0913 on methionine and other nucleophilic amino acids was specified in X! Tandem as variable modifications. Scaffold (version Scaffold_4.0.6.1, Proteome Software Inc.) was used to validate MS/MS based peptide and protein identifications. Peptide identifications were accepted if they exceeded specific database search engine thresholds. X! Tandem identifications required at least—Log (Expect Scores) scores of greater than 1.2 with a mass accuracy of 5 ppm. Protein identifications were accepted if they contained at least 2 identified peptides. Using the parameters above, the Decoy False Discovery Rate (1-DR) was calculated to be 1.1% on the protein level and 0.0% on the spectrum level.(42) Proteins that contained similar peptides and could not be differentiated based on MS/MS analysis alone were grouped to satisfy the principles of parsimony.

Colocalization experiments. Colocalization experiments were performed in live $HEK_{293}T$ cells with inducible cell surface GFP expression system. $HEK_{293}T$ cells were plated on poly-lysine coated chamber slides. Cells were induced to express GFP on the cell surface with addition of 1 μM/mL Dox (1000× stock in water) for 24 hour at the confluency around 25%. The cells were then treated with 100 ng/mL GFP-Fab-Cy3 (100× stock in PBS) for 1 hour. The labeled cells were washed with 10% FBS/DMEM (phenol red free) twice and were imaged using a Zeiss laser scanning microscope 710 with a 63× oil-immersion objective lens using Zen 2009 software (Carl Zeiss). Cy3 was excited using a 543 nm HeNe laser, and GFP was excited using a 488 nm Ar laser. The cells were imaged at 37° C. throughout the course of the experiment. Image analysis and quantification was performed using ImageJ (National Institutes of Health).

In vitro ADC cytotoxicity assay. BT474 cells were plated into black-sided, clear-bottom 96-well plates with 90 μL growth media per well. A 10× concentration working stock of WT-Fab, WT-Fab+free drug and ADC were prepared, and then titrated as 5-fold serial dilution to produce an 8-point dose response curves. Protein samples (10 μL) were added to each well with the confluency around 50% in duplicate. Cells were further incubated for 72 hours. Cytotoxicity was measured with One Solution Cell Proliferation MTS Assay (Promega Corporation) following manufacturer's instruction. Cell survival curves were plotted with OriginPro (OriginLab Corporation).

Enolase activity assay. Enzymatic activity of WT Yeast ENO 1 and its variants were measured with Synergy™ Mx Microplate Reader (BioTek). Protein samples (0.2 mg/mL) in 50 mM tris-acetic acid buffer (pH=7.8) were treated with 100 μM NaClO at room temperature for 1 hour in duplicate. The oxidation reactions were quenched by desalting twice with Bio-Spin Chromatography Columns (Bio-Rad). The activity of protein samples with or without oxidation treatment was measured by Enolase Activity Assay Kit (BioVision) according to manufacturer's instruction.

Yeast genome editing. *S. cerevisiae* strain BY4741 (201388; ATCC) was used as WT strain for genome editing. Knock out and mutation strains were generated by CRISPR-Cas9-mediated genome editing protocol as reported.(43) Briefly, for ENO2 knock out strain, yeast competent cell (50 μL) was transformed with 1.0 μg pCAS plasmid and 2.0 μg linear repair DNA using Frozen-EZ Yeast Transformation II™ Kit (Zymo Research) according to manufacturer's protocol. The transformed cells were plated onto YPG plates with antibiotics. Cells were grown overnight at 37° C. and then another 48 h at 30° C. The positive colonies ware confirmed by DNA sequencing. For ENO1-M171L (ENO2 null) strain, ENO2 knock out strain (losing pCAS9 plasmid) was used as mother strain for subsequent enolase 1 mutation.

Yeast growth curve measurement. Yeast growth curve was measured with Synergy™ Mx Microplate Reader (BioTek) with shaking at 30° C. using kinetics model. Yeast strains were grown to stationary phase in yeast nitrogen base medium with synthetic complete. Then the cells were diluted 1:50 into fresh yeast nitrogen base medium with or without treatment of 100 μM NaClO in duplicate. The absorbance at 600 nm was measured every 30 min.

Protein expression and purification. GFP-Fabs production: GFP-Fabs were produced using phage display methods and were constructed into a pSFV4 expression vector as previously described.(44). Methionine point mutations were incorporated by site-directed mutagenesis at heavy chain A114M, light chain V205M, and at the C-terminus of the light chain directly after the interchain disulfide. Recombinant Fabs were produced in C43 (DE3) Pro+ cells as previously described.(44) Briefly, cultures were grown to OD ~0.6 and induced with 0.2 mM IPTG at 30° C. overnight. Fabs were purified by protein A chromatography and buffer exchanged into PBS for subsequent storage and validation assays. For live cell application, endotoxin in recombinant Fabs solutions were removed by High Capacity Endotoxin Removal Spin Columns (Thermal Fisher Scientific).

Her-Fabs production: Light chain and heavy chain of Her-Fab were codon optimized(45) and constructed into a pComb3XSS expression vector as previously described. (46)

Methionine knock in mutations at the C-terminus of the light chain were incorporated directly after the interchain disulfide. Recombinant Her-Fabs were produced and purified by protein A chromatography as well. For ADC application, endotoxin in recombinant Fabs solutions were removed by High Capacity Endotoxin Removal Spin Columns (Thermal Fisher Scientific).

Yeast enolase 1 production: Yeast enolase 1 was amplified from yeast (S288C) genomic DNA and inserted into a pET28a expression vector with a 6× His tag at the N-terminus. Met 171 or 371 was converted to Leu using site-directed mutagenesis. The recombinant proteins were expressed in BL21(DE3)pLysS (Invitrogen) strain and purified according to previous papers.(47,48) The sequence alignment of enolase family proteins was perform by the Clustal Omega program.(49)

Octet BioLayer Interferometry binding assay. The purified GFP-Fabs were diluted with 0.05% tween 20+0.2% BSA/PBS to the concentration 300 nM. The Fab samples were immobilized on anti-Fab sensors (ForteBio) that bind the CH1-region of human Fab. The immobilized sensors were sampled with the serially diluted concentrations of recombinant GFP ligand (BioVision) in the Octet RED 384 system. The obtained results were fitted according to the protocol provided by the manufacturer.

Chemical Synthesis of Oxaziridine Probes.

N-ethyl-3-phenyl-1,2-oxaziridine-2-carboxamide (Ox2)

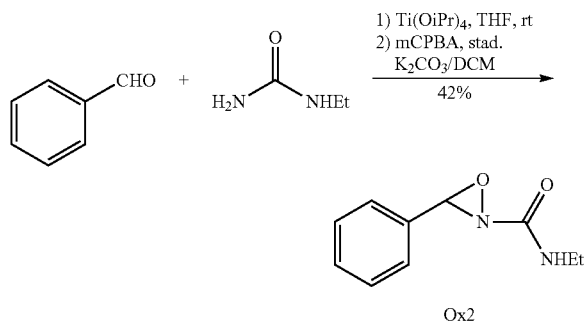

To a solution of benzaldehyde (1.21 mL, 12 mmol) and 1-ethylurea (880 mg, 10 mmol) in THF (20 mL) was added Ti(OiPr)$_4$ (3.2 mL, 11 mL) at r.t. After stirring overnight, the mixture was concentrated under vacuum to afford a residue. To a mixture solution of satd. K$_2$CO$_3$ (30 mL) and DCM (30 mL) was added meta-chloroperoxybenzoic acid (mCPBA, 6.9 g, 76% purity, 30 mmol) at r.t. After stirring for 10 min, a solution of the above residue in DCM (30 mL) was added slowly into the mixture at r.t. After stirring for another 6 h, water (100 mL) was added and the mixture was extracted with DCM for three times. The combined organic layer was then washed with brine, dried over Na$_2$SO$_4$, filtered and concentrated under vacuum to give a residue, which was purified by column chromatography (DCM/Et20, 100:1) to afford the Ox2 as a white solid (802 mg, 42%). $^1$H NMR (400 MHz, CDCl$_3$) δ 7.52-7.37 (m, 5H), 6.14 (brs, 1H), 4.99 (s, 1H), 3.40-3.23 (m, 2H), 1.19 (t, J=7.3 Hz, 3H). $^{13}$C NMR (101 MHz, CDCl$_3$) δ 162.23, 132.48, 131.06, 128.69, 128.03, 79.42, 35.45, 14.79. m/z HRMS (ESI) found [M+H]+193.0972, C$_{10}$H$_{13}$O$_2$N$_2$$^+$ requires 193.0972.

Ethyl 3-phenyl-1,2-oxaziridine-2-carboxylate (Ox1)

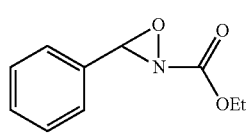

Ox1 was synthesized with the same procedure used in making Ox2 using ethyl carbamate in place of 1-ethylurea in 20% yield. $^1$H NMR (400 MHz, CDCl$_3$) δ 7.52-7.38 (m, 5H), 5.10 (s, 1H), 4.43-4.24 (m, 2H), 1.36 (t, J=7.2 Hz, 3H). $^{13}$C NMR (101 MHz, CDCl$_3$) δ 162.23, 132.07, 131.26, 128.78, 128.06, 78.29, 64.78, 14.19. m/z HRMS (ESI) found [M+H]$^+$ 216.0631, C$_{10}$H$_{11}$O$_3$NNa$^+$ requires 216.0631.

N-ethyl-3-phenyl-3-(trifluoromethyl)-1,2-oxaziridine-2-carboxamide (Ox3)

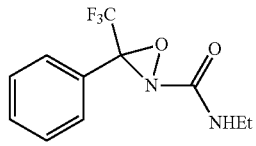

Ox3 was synthesized with the same procedure used in making Ox2 using 2,2,2-trifluoro-1-phenylethan-1-one in place of benzaldehyde in 10% yield. $^1$H NMR (400 MHz, CDCl$_3$) δ 7.58 (d, J=7.6 Hz, 2H), 7.50 (t, J=7.4 Hz, 1H), 7.42 (t, J=7.5 Hz, 2H), 5.82 (brs, 1H), 3.07-2.93 (m, 1H), 2.93-2.80 (m, 1H), 0.62 (t, J=7.2 Hz, 3H). $^{13}$C NMR (101 MHz, CDCl$_3$) δ 157.78, 131.51, 128.57, 128.25, 124.91, 120.90 (q, J=281.4 Hz), 82.29 (q, J=38.7 Hz), 35.10, 14.13. $^{19}$F NMR (376 MHz, CDCl$_3$) δ −76.82. m/z HRMS (ESI) found [M+H]$^+$ 261.0846, C11H$_{12}$O$_2$N$_2$F$_3$$^+$ requires 261.0845.

3-Phenyl-N-(prop-2-yn-1-yl)-1,2-oxaziridine-2-carboxamide (Ox4)

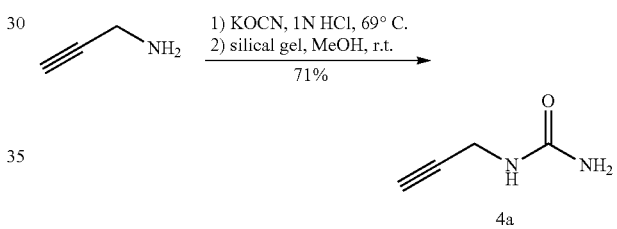

To a solution of propargylamine (3.2 mL, 50 mmol) in aqueous HCl solution (1.0 N, 50 mL) was added KOCN (16 g, 200 mmol) at r.t. After stirring overnight at 60° C., the mixture was cooled to 0° C. to give a white precipitate. After filtration, the solid was dissolved in MeOH (150 ml) and stirred with silica gel (25 g) for 6 h. The mixture was then filtered and concentrated under vacuum to give the desired urea 4a as a white solid (3.5 g, 71%) without further purification. $^1$H NMR (400 MHz, MeOD) δ 3.88 (d, J=2.5 Hz, 2H), 2.54 (t, J=2.5 Hz, 1H). $^{13}$C NMR (126 MHz, MeOD) δ 161.55, 81.63, 71.80, 30.18. m/z HRMS (ESI) found [M+H]$^+$ 99.0552, C$_4$H$_7$N$_2$O$^+$ requires 99.0553.

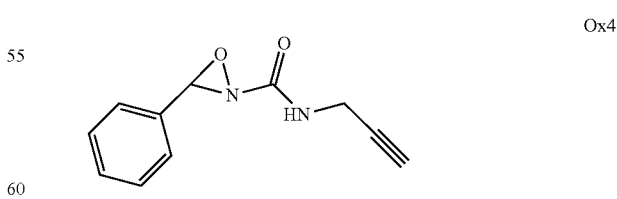

Ox4 was synthesized with the same procedure used in making Ox2 using 4a as substrate in place of 1-ethylurea in 21% yield. $^1$H NMR (400 MHz, CDCl$_3$) δ 7.52-7.35 (m, 5H), 6.26 (s, 1H), 5.04 (s, 1H), 4.09 (dt, J=5.4, 2.7 Hz, 2H), 2.31 (t, J=2.6 Hz, 1H). $^{13}$C NMR (101 MHz, CDCl$_3$) δ 162.05, 132.08, 131.14, 128.68, 128.02, 79.44, 78.42, 72.54, 30.21. m/z HRMS (ESI) found [M+H]+ 203.0813, $C_{11}H_{11}N_2O_2^+$ requires 203.0815.

3-Phenyl-N-(2-(prop-2-yn-1-yloxy)ethyl)-1,2-oxaziridine-2-carboxamide (Ox5)

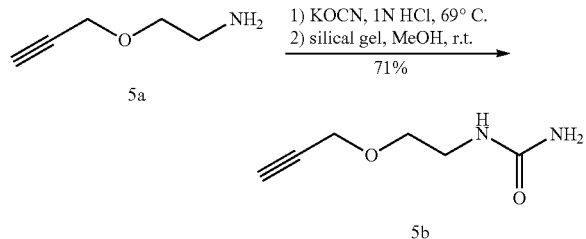

The amine 5a was synthesized according literature.(50) To a solution of amine 5a (1.9 g, 18.8 mmol) in aqueous HCl solution (1.0 N, 19 mL) was added KOCN (7.6 g, 94 mmol) at r.t. After stirring overnight at 60° C., the mixture was cooled to 0° C. The mixture was extracted with ethyl acetate repeatedly until full extraction which was determined by TLC analysis. The organic layer was dried over $Na_2SO_4$, filtered and concentrated under vacuum to give a residue. To a solution of the residue in MeOH (50 mL) was added silica gel (10 g) at r.t. After stirring for 6 h, the mixture was filtered and concentrated under vacuum to give the desired urea 5b as an oil (1.9 g, 71%). $^1$H NMR (400 MHz, MeOD) δ 4.19 (s, 2H), 3.58 (t, J=5.4 Hz, 2H), 3.35-3.29 (m, 2H), 2.87 (s, 1H). $^{13}$C NMR (126 MHz, CDCl$_3$) δ 162.19, 80.53, 75.95, 70.15, 58.90, 40.70. m/z HRMS (ESI) found [M+H]+ 143.0815, $C_6H_{11}N_2O_2^+$ requires 143.0815.

Ox5 was synthesized with the same procedure used in making Ox2 using 5b as substrate in place of 1-ethylurea in 33% yield. $^1$H NMR (400 MHz, CDCl$_3$) δ 7.48-7.32 (m, 5H), 5.00 (s, 1H), 4.15 (d, J=2.4 Hz, 2H), 3.67-3.57 (m, 2H), 3.52-3.42 (m, 2H), 2.48 (t, J=2.5 Hz, 1H). $^{13}$C NMR (101 MHz, CDCl$_3$) δ 162.44, 132.38, 131.01, 128.63, 127.98, 79.36, 79.30, 75.11, 68.08, 58.36, 40.14. m/z HRMS (ESI) found [M+Na]+ 269.0893, $C_{13}H_{14}N_2O_3Na^+$ requires 269.0897.

N-(3-azidopropyl)-3-phenyl-1,2-oxaziridine-2-carboxamide (Ox6)

To a solution of amine (250 mg, 2.5 mmol) in 1 N HCl (3 mL) was added KOCN (810 mg, 10.0 mmol). After stirring for 18 h at 60° C., the mixture was cooled to r.t. and extracted with DCM until full extraction which was determined by TLC analysis. The combined organic layer was dried over $Na_2SO_4$, filtered and concentrated under vacuum to give the urea as a white solid. To a solution of benzaldehyde (303 µL, 3.0 mmol) and the above urea in THF (10 mL) was added Ti(OiPr)$_4$ (1.0 mL, 3.5 mmol) at r.t. After stirring for 4 h, the mixture was concentrated under vacuum to afford a residue. To a mixture solution of satd. $K_2CO_3$ (15 mL) and DCM (15 mL) was added mCPBA (2.6 g, 55% purity, 7.5 mmol) at r.t. After stirring for 10 min, a solution of the above residue in DCM (15 ml) was added slowly into the mixture at r.t. After stirring for 15 h, water (100 mL) was added and the mixture was extracted with DCM for three times. The combined organic layer was then washed with brine, dried over $Na_2SO_4$, filtered and concentrated under vacuum to give a residue, which was purified by column chromatography (DCM/Et$_2$O, 50:1) to afford the oxaziridine Ox6 as an oil (138 mg, 22%). $^1$H NMR (400 MHz, CDCl$_3$) δ 7.52-7.31 (m, 5H), 6.46 (s, 1H), 4.99 (s, 1H), 3.41-3.25 (m, 4H), 1.85-1.73 (m, 2H). $^{13}$C NMR (101 MHz, CDCl$_3$) δ 162.50, 132.28, 131.06, 128.64, 127.94, 79.37, 49.06, 38.03, 28.55.

General Procedure for Coupling of Methionine and Oxaziridine

To a solution of methyl acetyl-L-methioninate (S1, 10.3 mg, 0.05 mmol) in d-MeOD/D$_2$O (0.25 mL/0.25 mL) was added oxaziridine Ox2 (10.6 mg, 0.055 mmol) at r.t. The conversion and ratio between NTP (S2) and OTP was monitored by ¹H NMR. After 10 min, the solvents were removed under vacuum to give a residue, which was purified by column chromatography (DCM/MeOH, 5:1) to afford the S2 (13.2 mg, 91%) as an oil. ¹H NMR (400 MHz, MeOD) δ 4.55 (td, J=8.5, 4.9 Hz, 1H), 4.55 (td, J=8.5, 4.9 Hz, 1H), 3.14 (q, J=7.2 Hz, 2H), 3.07-2.92 (m, 2H), 2.66 (s, 3H), 2.33-2.21 (m, 1H), 2.12-2.03 (m, 1H), 2.01 (s, 1.5H), 2.00 (s, 1.5H), 1.08 (t, J=7.2 Hz, 3H). ¹³C NMR (101 MHz, MeOD) δ 173.45, 172.84, 168.47, 53.00, 52.82, 52.47, 45.96, 45.74, 32.17, 31.97, 26.36, 26.28, 22.42, 22.38, 15.82. m/z HRMS (ESI) found [M+H]⁺ 292.1320, $C_{11}H_{22}N_3O_4S^+$ requires 292.1326.

The Stability of Redox Conjugation Product-Sulfimide

The stability of sulfimides were tested by treatment of sulfimides S2 with 5 mM TCEP or treatment of sulfimides S3 with 1 N HCl, 1 N NaOH or 80° C. in co-solvent (d-MeOD/D2O=1:1). The reactions were monitored by NMR after 1 h and 18 h and the reaction conversions were calculated based on NMR data. Sulfimide S3 can be protonated under strong acidic condition to its salt form S4, which is stable in aqueous solution.

N-ethylcarbamyl-S-methyl-S-phenyl sulfurimine
(S3)

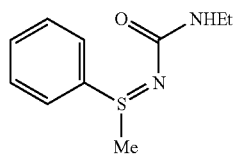

¹H NMR (500 MHz, MeOD) δ 7.81-7.75 (m, 2H), 7.62-7.54 (m, 3H), 3.18 (q, J=7.2, 5.9 Hz, 2H), 2.86 (s, 3H), 1.10 (t, J=7.2 Hz, 3H). ¹³C NMR (126 MHz, MeOD) δ 168.01, 139.36, 133.01, 130.91, 126.97, 36.78, 35.44, 15.89. m/z HRMS (ESI) found [M+H]⁺ 211.0987, $C_{10}H_{15}N_2OS^+$ requires 211.0900.

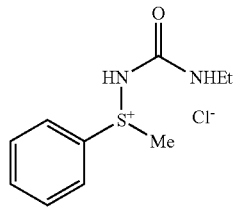

¹H NMR (400 MHz, MeOD/D2O) δ 8.02 (d, J=7.5 Hz, 2H), 7.84 (t, J=7.4 Hz, 1H), 7.75 (t, J=7.7 Hz, 2H), 3.60 (s, 3H), 3.17 (q, J=7.2 Hz, 2H), 1.08 (t, J=7.2 Hz, 3H).

REFERENCES

1 Stipanuk, M. H. Sulfur Amino Acid Metabolism: Pathways for Production and Removal of Homocysteine and Cysteine. Annual Review of Nutrition 24, 539-577, (2004).
2 Lehninger, A., Nelson, D. & Cox, M. Lehninger Principles of Biochemistry. (W. H. Freeman, 2008).
3 Levine, R. L., Mosoni, L., Berlett, B. S. & Stadtman, E. R. Methionine Residues as Endogenous Antioxidants in Proteins. Proceedings of the National Academy of Sciences 93, 15036-15040, (1996).
4 Giles, N. M. et al. Metal and Redox Modulation of Cysteine Protein Function. Chemistry & Biology 10, 677-693, (2003).
5 Hess, D. T., Matsumoto, A., Kim, S.-O., Marshall, H. E. & Stamler, J. S. Protein S-Nitrosylation: Purview and Parameters. Nature Reviews Molecular Cell Biology 6, 150-166, (2005).
6 D'Autreaux, B. & Toledano, M. B. ROS as Signalling Molecules: Mechanisms That Generate Specificity in ROS Homeostasis. Nature Reviews Molecular Cell Biology 8, 813-824, (2007).
7 Dickinson, B. C. & Chang, C. J. Chemistry and Biology of Reactive Oxygen Species in Signaling or Stress Responses. Nature Chemical Biology 7, 504-511, (2011).
8 Hang, H. C. & Linder, M. E. Exploring Protein Lipidation with Chemical Biology. Chemical Reviews 111, 6341-6358, (2011).
9 Paulsen, C. E. & Carroll, K. S. Cysteine-Mediated Redox Signaling: Chemistry, Biology, and Tools for Discovery. Chemical Reviews 113, 4633-4679, (2013).
10 Kabil, O., Vitvitsky, V. & Banerjee, R. Sulfur as a Signaling Nutrient Through Hydrogen Sulfide. Annual Review of Nutrition 34, 171-205, (2014).
11 Stephanopoulos, N. & Francis, M. B. Choosing an Effective Protein Bioconjugation Strategy. Nature Chemical Biology 7, 876-884, (2011).
12 Spicer, C. D. & Davis, B. G. Selective Chemical Protein Modification. Nature Communications 5, (2014).
13 Krall, N., da Cruz, F. P., Boutureira, O. & Bernardes, G. J. L. Site—Selective Protein-Modification Chemistry for Basic Biology and Drug Development. Nature Chemistry 8, 103-113, (2016).
14 Volgraf, M. et al. Allosteric Control of an Ionotropic Glutamate Receptor with an Optical Switch. Nature Chemical Biology 2, 47-52, (2006).
15 Weerapana, E. et al. Quantitative Reactivity Profiling Predicts Functional Cysteines in Proteomes. Nature 468, 790-795, (2010).
16 Hubbell, W. L., López, C. J., Altenbach, C. & Yang, Z. Technological Advances in Site-Directed Spin Labeling of Proteins. Current Opinion in Structural Biology 23, 725-733, (2013).
17 Mizukami, S., Hori, Y. & Kikuchi, K. Small-Molecule-Based Protein-Labeling Technology in Live Cell Studies: Probe-Design Concepts and Applications. Accounts of Chemical Research 47, 247-256, (2014).
18 Brewer, T. F., Garcia, F. J., Onak, C. S., Carroll, K. S. & Chang, C. J. Chemical Approaches to Discovery and Study of Sources and Targets of Hydrogen Peroxide Redox Signaling Through NADPH Oxidase Proteins. Annual Review of Biochemistry 84, 765-790, (2015).
19 Serafimova, I. M. et al. Reversible Targeting of Noncatalytic Cysteines with Chemically Tuned Electrophiles. Nature Chemical Biology 8, 471-476, (2012).
20 Ostrem, J. M., Peters, U., Sos, M. L., Wells, J. A. & Shokat, K. M. K-Ras(G12C) Inhibitors Allosterically Control GTP Affinity and Effector Interactions. Nature 503, 548-551, (2013).
21 Liu, Q. et al. Developing Irreversible Inhibitors of the Protein Kinase Cysteinome. Chemistry & Biology 20, 146-159, (2013).
22 Agarwal, P. & Bertozzi, C. R. Site-Specific Antibody-Drug Conjugates: The Nexus of Bioorthogonal Chemistry, Protein Engineering, and Drug Development. Bioconjugate Chemistry 26, 176-192, (2015).

23 Nomura, D. K., Dix, M. M. & Cravatt, B. F. Activity-Based Protein Profiling for Biochemical Pathway discovery in Cancer. Nature Review Cancer 10, 630-638, (2010).

24 Sanman, L. E. & Bogyo, M. Activity-Based Profiling of Proteases. Annual Review of Biochemistry 83, 249-273, (2014).

25 Leung, D., Hardouin, C., Boger, D. L. & Cravatt, B. F. Discovering Potent and Selective Reversible Inhibitors of Enzymes in Complex Proteomes. Nature Biotechnology 21, 687-691, (2003).

26 Johnson, J. A., Lu, Y. Y., Van Deventer, J. A. & Tirrell, D. A. Residue-Specific Incorporation of Non-Canonical Amino Acids into Proteins: Recent Developments and Applications. Current Opinion in Chemical Biology 14, 774-780, (2010).

27 McKay, Craig S. & Finn, M. G. Click Chemistry in Complex Mixtures: Bioorthogonal Bioconjugation. Chemistry & Biology 21, 1075-1101, (2014).

28 Boutureira, O. & Bernardes, G. J. L. Advances in Chemical Protein Modification. Chemical Reviews 115, 2174-2195, (2015).

29 Koniev, O. & Wagner, A. Developments and Recent Advancements in the Field of Endogenous Amino Acid Selective Bond Forming Reactions for Bioconjugation. Chemical Society Reviews 44, 5495-5551, (2015).

30 Zhang, C. et al. π-Clamp-Mediated Cysteine Conjugation. Nature Chemistry 8, 120-128, (2016).

31 Vinogradova, E. V., Zhang, C., Spokoyny, A. M., Pentelute, B. L. & Buchwald, S. L. Organometallic Palladium Reagents for Cysteine Bioconjugation. Nature 526, 687-691, (2015).

32 Wright, T. H. et al. Posttranslational Mutagenesis: A Chemical Strategy for Exploring Protein Side-Chain Diversity. Science, (2016).

33 Yang, A. et al. A Chemical Biology Route to Site-Specific Authentic Protein Modifications. Science, (2016).

34 Gladyshev, V. N. Symposium 6: Trace Elements S6-1-Selenium and Methionine Sulfoxide Reduction. Free Radical Biology and Medicine 75, Supplement 1, S8-S9, (2014).

35 Kaya, A., Lee, B. C. & Gladyshev, V. N. Regulation of Protein Function by Reversible Methionine Oxidation and the Role of Selenoprotein MsrB 1. Antioxidants & Redox Signaling 23, 814-822, (2015).

36 Hung, R.-J. et al. Mical Links Semaphorins to F-Actin Disassembly. Nature 463, 823-827, (2010).

37 Hung, R.-J., Pak, C. W. & Terman, J. R. Direct Redox Regulation of F-Actin Assembly and Disassembly by Mical. Science 334, 1710-1713, (2011).

38 Lee, Byung C. et al. MsrB1 and MICALs Regulate Actin Assembly and Macrophage Function via Reversible Stereoselective Methionine Oxidation. Molecular Cell 51, 397-404, (2013).

39 Moskovitz, J. et al. Methionine Sulfoxide Reductase (MsrA) is a Regulator of Antioxidant Defense and Lifespan in Mammals. Proceedings of the National Academy of Sciences 98, 12920-12925, (2001).

40 Lewis, A. K. et al. Oxidation Increases the Strength of the Methionine-Aromatic Interaction. Nature Chemical Biology 12, 860-866, (2016).

41 Kramer, J. R. & Deming, T. J. Reversible Chemoselective Tagging and Functionalization of Methionine Containing Peptides. Chemical Communications 49, 5144-5146, (2013).

42 Shannon, D. A. & Weerapana, E. Covalent Protein Modification: The Current Landscape of Residue-Specific Electrophiles. Current Opinion in Chemical Biology 24, 18-26, (2015).

43 Craig, R. & Beavis, R. C. TANDEM: Matching Proteins with Tandem Mass Spectra. Bioinformatics 20, 1466-1467, (2004).

44 Junutula, J. R. et al. Site-Specific Conjugation of A Cytotoxic Drug to An Antibody Improves The Therapeutic Index. Nature Biotechnology 26, 925-932, (2008).

45 Speers, A. E. & Cravatt, B. F. A Tandem Orthogonal Proteolysis Strategy for High-Content Chemical Proteomics. Journal of the American Chemical Society 127, 10018-10019, (2005).

46 Fothergill-Gilmore, L. A. & Michels, P. A. M. Evolution of Glycolysis. Progress in Biophysics and Molecular Biology 59, 105-235, (1993).

47 Vander Heiden, M. G., Cantley, L. C. & Thompson, C. B. Understanding the Warburg Effect: The Metabolic Requirements of Cell Proliferation. Science 324, 1029-1033, (2009).

48 Leonard, P. G. et al. SF2312 is a Natural Phosphonate Inhibitor of Enolase. Nature Chemical Biology advance online publication, (2016).

49 Szychowski, J. et al. Cleavable Biotin Probes for Labeling of Biomolecules via Azide-Alkyne Cycloaddition. Journal of the American Chemical Society 132, 18351-18360, (2010).

50 Woo, C. M., Iavarone, A. T., Spiciarich, D. R., Palaniappan, K. K. & Bertozzi, C. R. Isotope-Targeted Glycoproteomics (IsoTaG): A Mass-Independent Platform for Intact N- and O-glycopeptide Discovery and Analysis. Nature Methods 12, 561-567, (2015).

51 Ryan, O. W. et al. Selection of Chromosomal DNA Libraries Using a Multiplex CRISPR System. eLife 3, e03703, (2014).

52. D. T. Hess, A. Matsumoto, S.-O. Kim, H. E. Marshall, J. S. Stamler, Protein S-nitrosylation: Purview and parameters. Nat. Rev. Mol. Cell Biol. 6, 150-166 (2005).

53. B. D'Autréaux, M. B. Toledano, ROS as signalling molecules: Mechanisms that generate specificity in ROS homeostasis. Nat. Rev. Mol. Cell Biol. 8,813-824 (2007).

54. B. C. Dickinson, C. J. Chang, Chemistry and biology of reactive oxygen species in signaling or stress responses. Nat. Chem. Biol. 7, 504-511 (2011).

55. H. C. Hang, M. E. Linder, Exploring protein lipidation with chemical biology. Chem. Rev. 111, 6341-6358 (2011).

56. O. Kabil, V. Vitvitsky, R. Banerjee, Sulfur as a signaling nutrient through hydrogen sulfide. Annu. Rev. Nutr. 34, 171-205 (2014).

57. M. Volgraf, P. Gorostiza, R. Numano, R. H. Kramer, E. Y. Isacoff, D. Trauner, Allosteric control of an ionotropic glutamate receptor with an optical switch. Nat. Chem. Biol. 2, 47-52 (2006).

58. J. A. Johnson, Y. Y. Lu, J. A. Van Deventer, D. A. Tirrell, Residue-specific incorporation of non-canonical amino acids into proteins: Recent developments and applications. Curr. Opin. Chem. Biol. 14, 774-780 (2010).

59. N. Stephanopoulos, M. B. Francis, Choosing an effective protein bioconjugation strategy. Nat. Chem. Biol. 7, 876-884 (2011).

60. W. L. Hubbell, C. J. López, C. Altenbach, Z. Yang, Technological advances in site-directed spin labeling of proteins. Curr. Opin. Struct. Biol. 23, 725-733 (2013).

61. Q. Liu, Y. Sabnis, Z. Zhao, T. Zhang, S. J. Buhrlage, L. H. Jones, N. S. Gray, Developing irreversible inhibitors of the protein kinase cysteinome. Chem. Biol. 20, 146-159 (2013).
62. C. S. McKay, M. G. Finn, Click chemistry in complex mixtures: Bioorthogonal bioconjugation. Chem. Biol. 21, 1075-1101 (2014).
63. O. Koniev, A. Wagner, Developments and recent advancements in the field of endogenous amino acid selective bond forming reactions for bioconjugation. Chem. Soc. Rev. 44, 5495-5551 (2015).
64. N. Krall, F. P. da Cruz, O. Boutureira, G. J. L. Bernardes, Site-selective protein-modification chemistry for basic biology and drug development. Nat. Chem. 8, 103-113 (2016).
65. P. J. Vithayathil, F. M. Richards, Modification of the methionine residue in the peptide component of ribonuclease-S. J. Biol. Chem. 235, 2343-2351 (1960).
66. C. Kleanthous, J. R. Coggins, Reversible alkylation of an active site methionine residue in dehydroquinase. J. Biol. Chem. 265, 10935-10939 (1990). Medline
67. J. R. Kramer, T. J. Deming, Preparation of multifunctional and multireactive polypeptides via methionine alkylation. Biomacromolecules 13, 1719-1723 (2012).
68. T. L. Gilchrist, C. J. Moody, The chemistry of sulfilimines Chem. Rev. 77, 409-435 (1977).
69. K. S. Williamson, D. J. Michaelis, T. P. Yoon, Advances in the chemistry of oxaziridines. Chem. Rev. 114, 8016-8036 (2014).

The invention claimed is:

1. A redox-activated chemical tagging (ReACT) method for functionalization of a protein having a surface accessible methionine residue, the method comprising contacting the protein in a non-denatured state with a urea oxaziridine in a buffered aqueous environment under conditions wherein the protein remains non-denatured and the urea oxaziridine directly functionalizes the protein by converting the surface-accessible methionine residue of the protein to the corresponding sulfimide conjugation product, without converting any surface inaccessible methionine residues of the protein, wherein the urea oxaziridine has the structure:

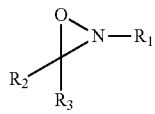

wherein:
$R_1$ is $-C(O)NHR_8$, and $R_8$ is $C_{1-6}$ alkyl optionally substituted with $C_{2-6}$ alkynyl, $C_{2-6}$ alkynyloxy, or $-N_3$;
$R_2$ is H, $C_{1-6}$ alkyl, or $C_{1-6}$ haloalkyl; and
$R_3$ is phenyl.

2. The method of claim 1, further comprising functionalizing the conjugation product with a payload.

3. The method of claim 1, further comprising functionalizing the conjugation product with a payload selected from the group consisting of a polyethylene glycol (PEG), a drug, a label, and a biomolecule selected from a DNA, an RNA, a lipid and a sugar.

4. The method of claim 1, further comprising functionalizing the conjugation product with a payload, wherein the payload is a polyethylene glycol (PEG) and the protein is a therapeutic protein.

5. The method of claim 1, further comprising functionalizing the conjugation product with a payload, wherein the payload is a drug and the protein is an antibody.

6. The method of claim 1, wherein the urea oxaziridine comprise a bioorthogonal alkyne group.

7. The method of claim 1, wherein the urea oxaziridine comprise a bioorthogonal alkyne group and the method further comprise functionalizing the conjugation product with a payload.

8. The method of claim 1, wherein the urea oxaziridine comprise a bioorthogonal alkyne group and the method further comprise functionalizing the conjugation product with a payload-azide through a copper-catalyzed azide-alkyne cycloaddition (CuAAC) reaction.

9. The method of claim 1, wherein the buffered aqueous environment is biocompatible.

10. The method of claim 1, wherein the buffered aqueous environment is phosphate buffered saline (PBS).

* * * * *